Jan. 7, 1975 K. K. MESERVE Plant Pat. 3675
ILEX BLUE PRINCESS PLANT
Filed Aug. 9, 1973
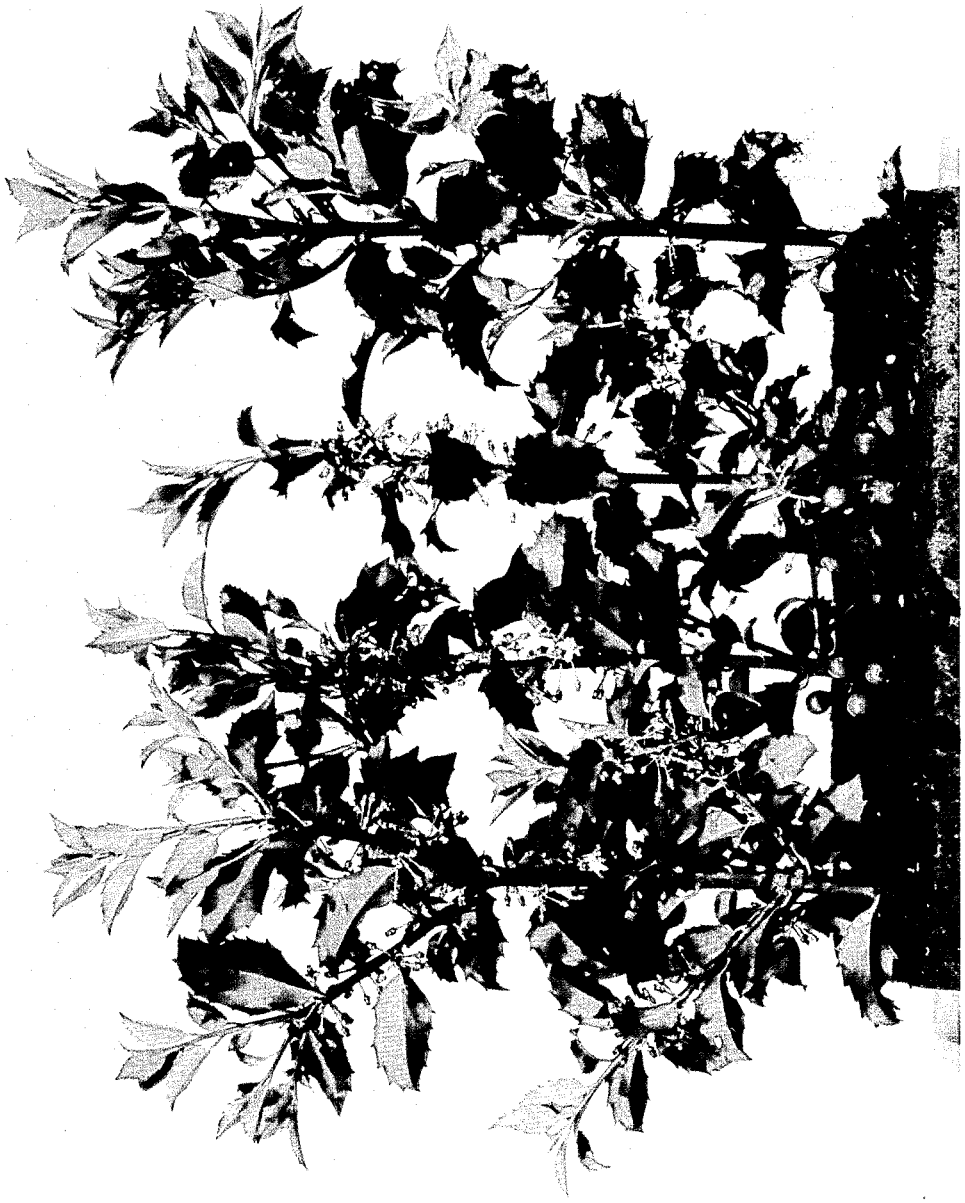

United States Patent Office

Plant Pat. 3,675
Patented Jan. 7, 1975

3,675

ILEX BLUE PRINCESS PLANT

Kathleen K. Meserve, St. James, N.Y., assignor to The Conard-Pyle Company, West Grove, Pa.

Filed Aug. 9, 1973, Ser. No. 387,041
Int. Cl. A01h *5/00*
U.S. Cl. Plt.—65 1 Claim

ABSTRACT OF THE DISCLOSURE

A new and distinct variety of Ilex which was originated by crossing *Ilex rugosa* with *Ilex aquifolium.*

SUMMARY OF THE INVENTION

The present invention relates to a new and distinct variety of Ilex which was originated by me by crossing *Ilex rugosa* with *Ilex aquifolium.*

The objective of my breeding was to create a decorative shrub of the genus Ilex with glossy, evergreen leaves bearing a profusion of red berries and with greater tolerance to cold than those heretofore known to exist.

As a result of this breeding, I have attained my objective and produced a new, distinct and improved Ilex which is distinguished from its parents and all other Ilex of which I am aware, as evidenced by the following unique combination of characteristics which are outstanding therein:

1. A vigorous, broad, densely branched, attractive and decorative evergreen shrub;
2. Flowers borne abundantly in May and moderately in June, July, August, September and October;
3. A shrub which produces unusual quantities of bright red berries, often in clusters;
4. Fruit sets more or less continuously from each flowering with the berries maturing a bright red in the order of the flowering;
5. Berries borne on longer stems than other Ilex making them more conspicuous and highly decorative;
6. Foliage more spiny and more wavy than other Ilex of the same parentage;
7. Leaves and branches whose color together give a unique and distinctive overall bluish-purple color effect to the plant;
8. Tolerance to winter cold and fluctuations superior to *Ilex aquifolium* varieties: "Brownell Special," "Everett," "Essen," "Firecracker" and "New York Botanic Garden #2" when grown under similar conditions at St. James, N.Y.;
9. Leaves with a slight reddish cast during winter months; and
10. Root hardiness superior to *Ilex crenata compacta,* Ilex × "Nellie Stevens," Ilex × "Dr. Kassab," *Ilex crenata* "Helleri," *Ilex crenata* "Hetzi," *Ilex crenata* "National," *Ilex crenata* "Compacta," *Ilex crenata* "Buxifolia," *Ilex Opaca* "New Jersey Special," Ilex × "Lydia Moris," Ilex × "Edward T. Stevens," Ilex × "John Morris," *Ilex cornuta* "National," and *Ilex aquifolium* "New York Botanic #2" all of which died except "New York Botanic Garden #2" which was seriously injured but was not killed when overwintered in containers above ground at West Grove, Pa., while my present invention survived without injury.

Asexual reproduction of my new variety by cuttings has been accomplished at St. James, N.Y., and at West Grove, Pa., and shows that its distinguishing characteristics are fixed and stable and are transmitted through succeeding propagations.

BRIEF DESCRIPTION OF DRAWING

The accompanying drawing shows typical specimens of my new variety of plant, some with flowers, and as depicted in color as nearly true as is reasonably possible to make the same in a color illustration of this character.

DETAILED DESCRIPTION OF DISCLOSURE

The following is a detailed description of my new variety, with color terminology in accordance with the Royal Horticultural Society Colour Chart of The Royal Horticultural Society, London, England:

Type: Hardy, tall, outdoor shrub; for garden decoration and general landscape use.

Parentage: *Ilex rugosa* × *Ilex aquifolium.* Parents of the first cross were unnamed selections of *Ilex aquifolium* and *Ilex rugosa.*

Class: Ilex × meserveae. Cross made in May 1952; seed sown in October 1952; germination in April 1954; selection made in 1958.

Locality where grown and observed: St. James, N.Y., and West Grove, Pa.

Propagation: It does hold its distinguishing characteristics through succeeding propagations by cuttings.

Flowers: Pistillate flowers are borne several to the stem, in rounded clusters, on normal, medium stems. Flowers are abundant outdoors in May and produced in moderate quantities continuously through the growing season.

*Bud.*—Flowers are carried on a medium length, medium diameter, stiff peduncle, light green, of the Color Group 146D. Peduncle is smooth. Before the calyx breaks, the size is small, buds are short, globular and without foliaceous appendages. As calyx breaks, the color is Group 56D. As the first petal opens, the buds are small, globular with Color Group 56D shaded lightly with 54D on the outside, and Color Group 56D on the inside. It does open up well.

Bloom: Blooms are small to medium in size—6.25 mm. in diameter. Petalage is single—4 and occasionally 5 petals; they are arranged regularly with 4 petals joined together in center. Form is cupped at first; becoming flat; petals remaining at first loosely cupped inward. Petals are thin, and satiny on inside and outside. Color: Outside surface: Color Group 56D. Inside surface: Color Group 56D, shaded lightly with 54D. Petals drop off cleanly. Flowers last on the bush in the garden 1 to 2 days in May.

Reproductive organs:

*Pistils.*—4.

*Styles.*—Even, medium long, medium heavy, separated, Color Group 56D.

*Stigma.*—White.

*Ovaries.*—All protruding from receptacle.

*Fruit.*—Round, 7 mm. to 9 mm. in diameter borne freely along the stems on peduncles 5 mm. to 12 mm. in length. Color is Group 46B, shiny with medium thick fleshy walls.

Foliage:

*Leaves.*—Simple, occurring abundantly, alternately arranged, of medium size, glossy, moderately heavy and somewhat crinkled. Leaves are attached by petioles 0.5 to 0.6 mm. in length. Leaves are ovate acuminate with base often obtuse and occasionally round. Mature leaves near the midpoint of a branch vary in width from 2.5 mm. to 2.9 mm. and vary in length from 4.0 mm. to 4.8 mm. measured to the tips of spines. The number of spines varies from 14 to 21. Color: Young Upper Surface: Color Group 143A. Under Surface: Color Group 146B.

*Young Foliage.*—Upper Surface: Very glossy, Color

Group 200C. Lower Surface: Dull, Color Group 147B.

*Old Foliage (growth from previous year).*— Upper Surface: Very glossy, Color Group 147A. Lower Surface: Dull, Color Group 147B.

*Young Stems.*—Dull, Color Group 200A.

*Old Stems (growth from the previous year).*—Dull, Color Group 147B. Old stems have diamond shaped spots: Color Group 201B. Light fruit bearing stems: Dull, Color Group 148A.

Berries: Bright, Color Group 46B. 7 to 9 mm. in diameter.

I claim:

1. A new and distinct variety of Ilex plant, substantially as herein shown and described, characterized particularly as to novelty by the unique combination of a vigorous, broad, densely branched decorative plant producing an abundance of pistillate flowers, bearing bright red fruit on stems longer than other Ilex and flowering through the growing season with bright red fruit maturing in the order of the flowering, the plant bearing leaves of shiny, rich green often turning slightly reddish in winter, the leaves and branches being of a color when taken in combination giving the plant a bluish-purple cast, and the plant having more cold tolerance than other red berried evergreen Ilex.

References Cited

UNITED STATES PATENTS

P.P. 2,434 8/1964 Meserve ---------- Plants—65

ROBERT E. BAGWILL, Primary Examiner